United States Patent [19]

Chan

[11] Patent Number: 5,891,150
[45] Date of Patent: Apr. 6, 1999

[54] APPARATUS AND METHOD FOR FIXING A LIGAMENT IN A BONE TUNNEL

[76] Inventor: Kwan-Ho Chan, 4803 First Pl., Lubbock, Tex. 79416

[21] Appl. No.: 759,551

[22] Filed: Dec. 4, 1996

[51] Int. Cl.[6] .................................................. A61B 17/56
[52] U.S. Cl. ............................................. 606/96; 606/98
[58] Field of Search ................................ 606/73, 72, 61, 606/60, 96, 86, 65, 66, 98, 80, 79

[56] References Cited

U.S. PATENT DOCUMENTS

| | | | |
|---|---|---|---|
| Re. 34,871 | 3/1995 | McGuire et al. | 606/73 |
| 2,081,293 | 5/1937 | Davis | 606/73 |
| 2,270,188 | 1/1942 | Longfellow | 606/73 |
| 3,973,277 | 8/1976 | Semple et al. | |
| 4,901,711 | 2/1990 | Goble et al. | |
| 4,985,032 | 1/1991 | Goble . | |
| 5,004,474 | 4/1991 | Fronk et al. | |
| 5,067,962 | 11/1991 | Campbell et al. | |
| 5,112,337 | 5/1992 | Paulos et al. | 606/96 |
| 5,147,362 | 9/1992 | Goble . | |
| 5,152,764 | 10/1992 | Goble . | |
| 5,154,720 | 10/1992 | Trott et al. | |
| 5,163,940 | 11/1992 | Bourque | 606/96 |
| 5,180,382 | 1/1993 | Frigg et al. | 606/65 |
| 5,266,075 | 11/1993 | Clark et al. | |
| 5,282,802 | 2/1994 | Mahoney, III | 606/72 |
| 5,350,380 | 9/1994 | Goble et al. | |
| 5,354,299 | 10/1994 | Coleman | 606/73 |
| 5,354,300 | 10/1994 | Goble et al. | |
| 5,356,435 | 10/1994 | Thein . | |
| 5,376,119 | 12/1994 | Zimmermann et al. | |
| 5,393,302 | 2/1995 | Clark et al. | |
| 5,397,356 | 3/1995 | Goble et al. | 623/13 |
| 5,431,651 | 7/1995 | Goble . | |
| 5,458,602 | 10/1995 | Goble et al. | 606/96 |
| 5,492,442 | 2/1996 | Lasner | 411/426 |

OTHER PUBLICATIONS

DePuy brochure "Bohlman Pins", 1 page, Dec. 1943.
"TransFix ACL Reconstruction", Arthrex, 1997, 23 pages.
"U–Shaped Drill Guide", Arthrotek, 1994, 7 pages.
Wolf, "SemiFix ACL Reconstruction", Arthrex, 1995, pp. 1–21.
"Tunneloc Bone Mulch Screw Technique", Arthrotek (1994 or later), pp. 1–9.
"Frontier ACL Reconstruction Guide System", DePuy ProSource, 1996.
"Optimal Tibial Tunnel Placement Referencing The O.T.B. (Over The Back) Position", DePuy ProSource (1995 or later).

*Primary Examiner*—Guy V. Tucker
*Attorney, Agent, or Firm*—Pandiscio & Pandiscio

[57] ABSTRACT

There is presented a drill guide assembly for forming a transverse guide hole in a bone, the guide hole being adapted to receive a transverse screw, the guide hole intersecting a tunnel formed in the bone and adapted to receive a body to be retained in the tunnel and to receive the screw transversely of the body to secure the body in the tunnel. The drill guide assembly comprises a track member of an elongated curved configuration, the track member having a bore extending widthwise therethrough, and a curved slide track extending lengthwise thereof, a boom member having a first portion of an elongated curved configuration slidably disposed in the slide track of the track member, and a second portion for retaining a drill bit. The assembly further includes a stem member for disposition in the track member bore, the stem member having an elongated stem portion for extending into the tunnel, and a guide member for attachment to a distal end of the stem portion, the guide member having a recess therein for receiving a distal end of a drill bit retained in the boom member second portion.

16 Claims, 12 Drawing Sheets

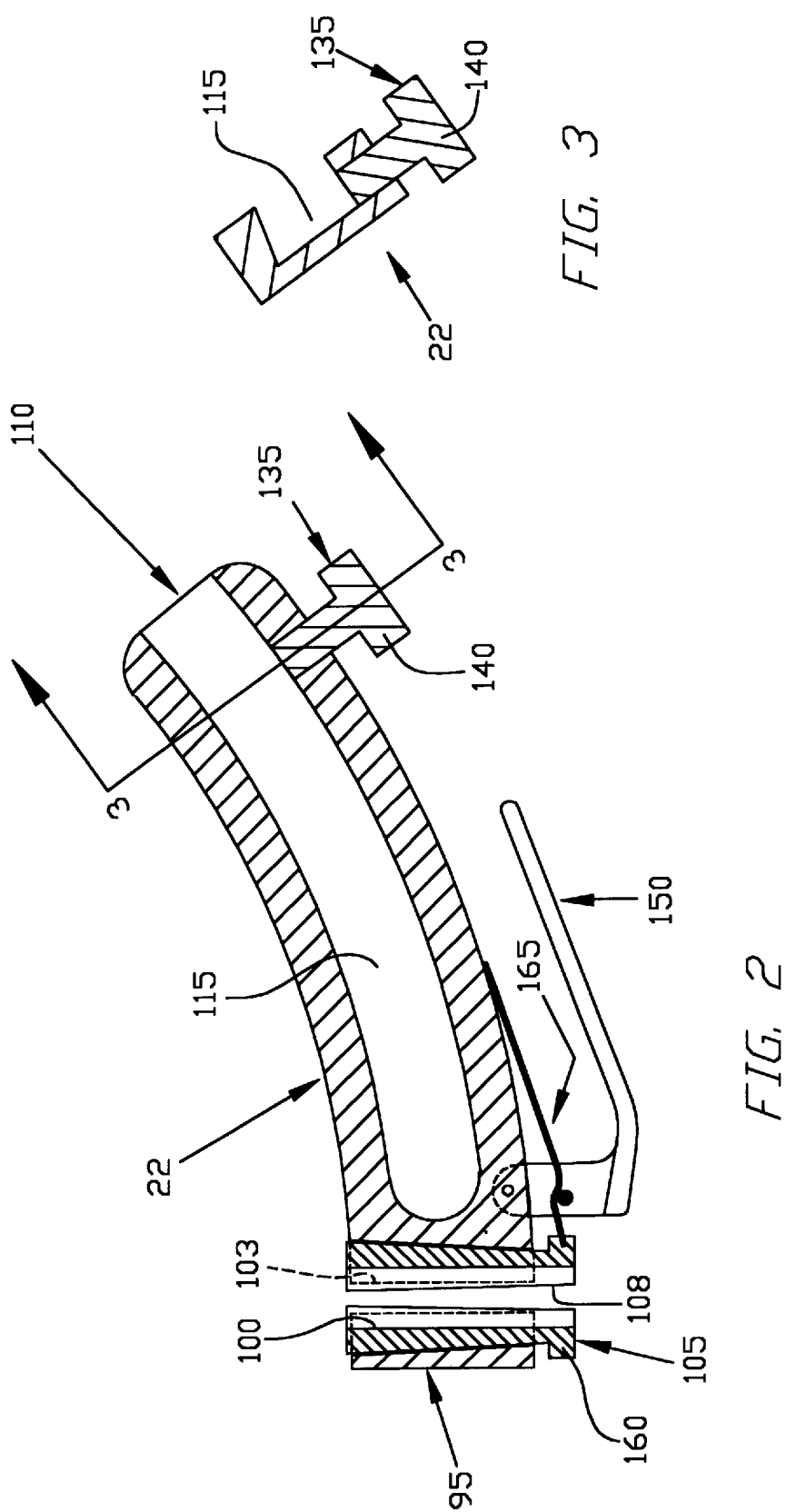

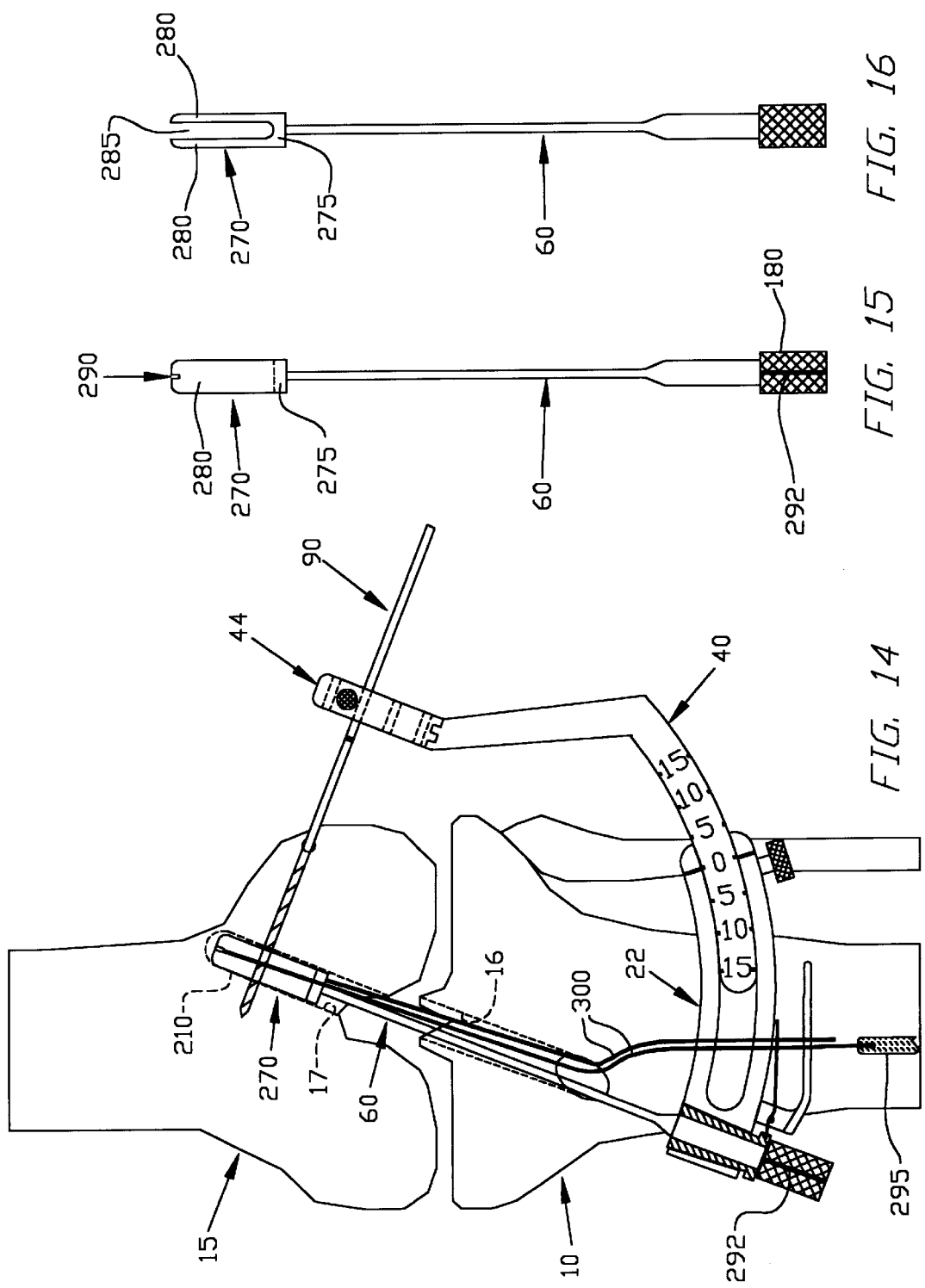

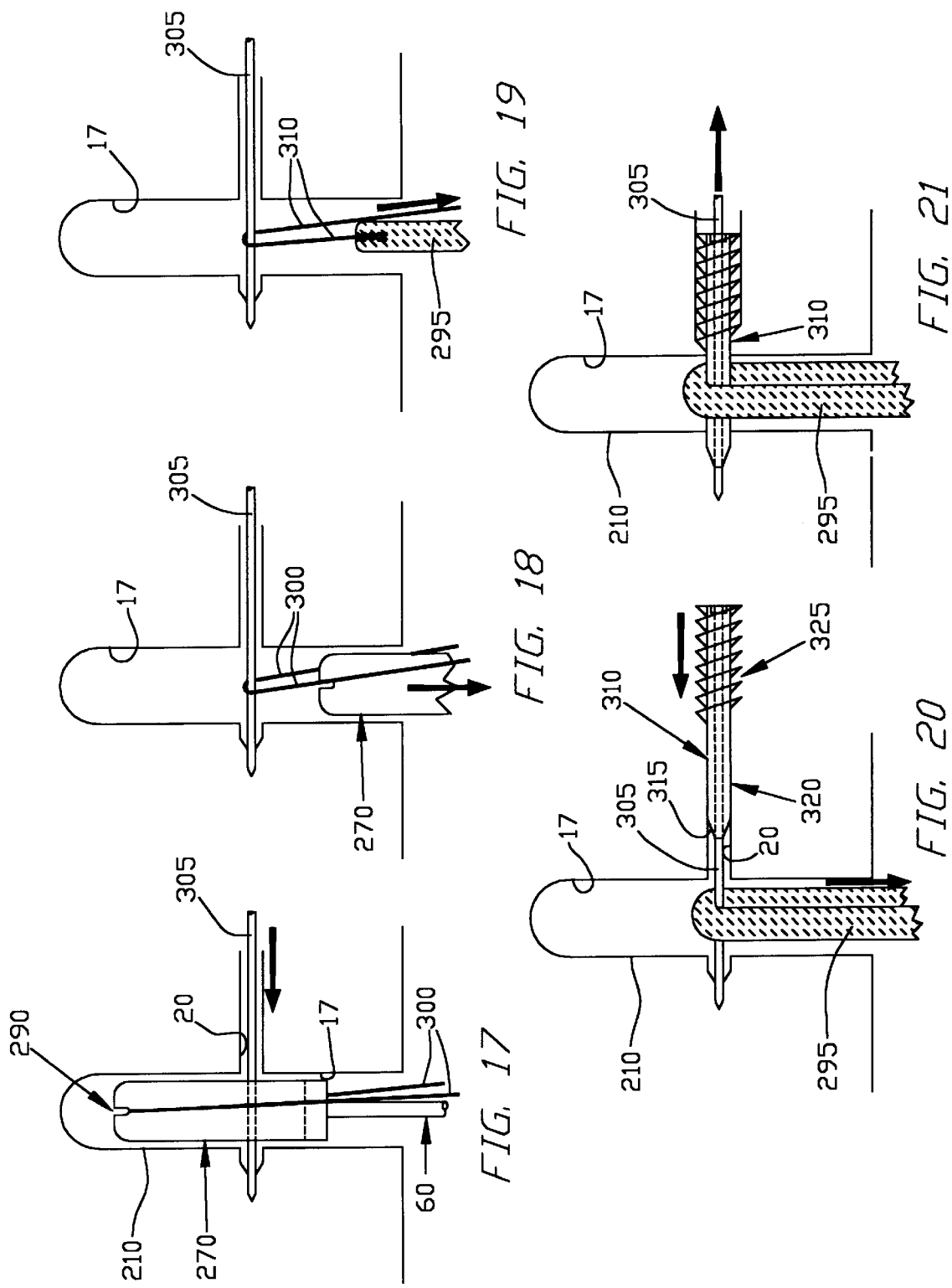

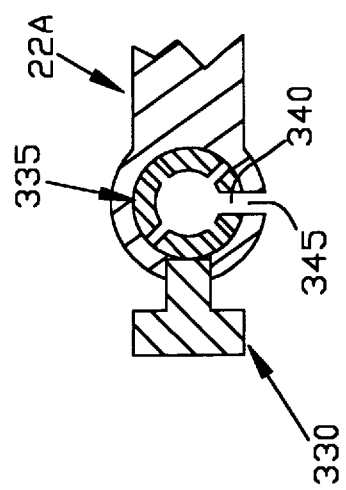
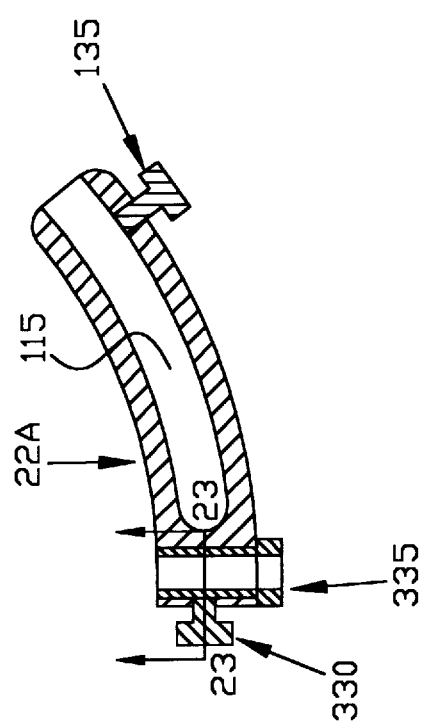

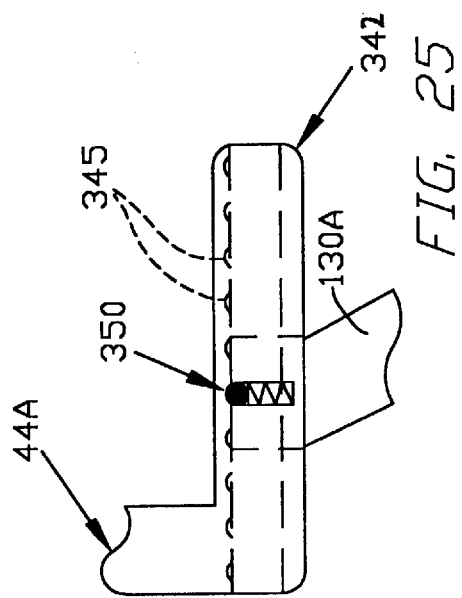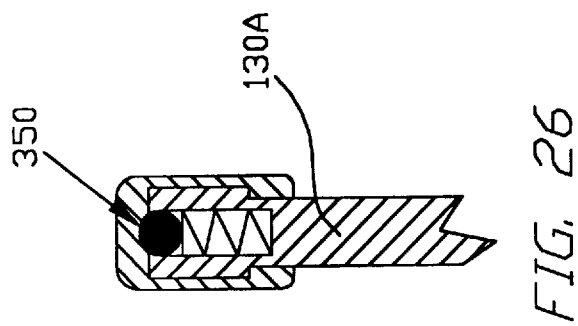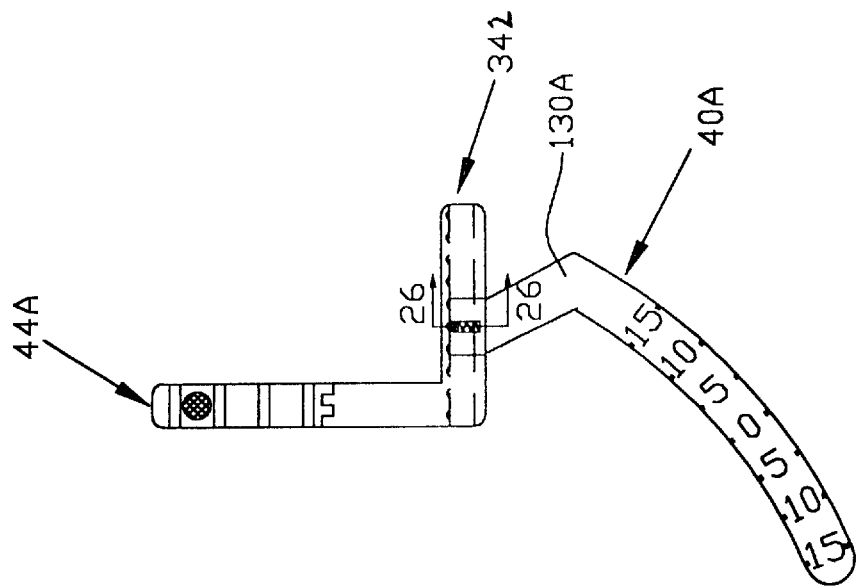

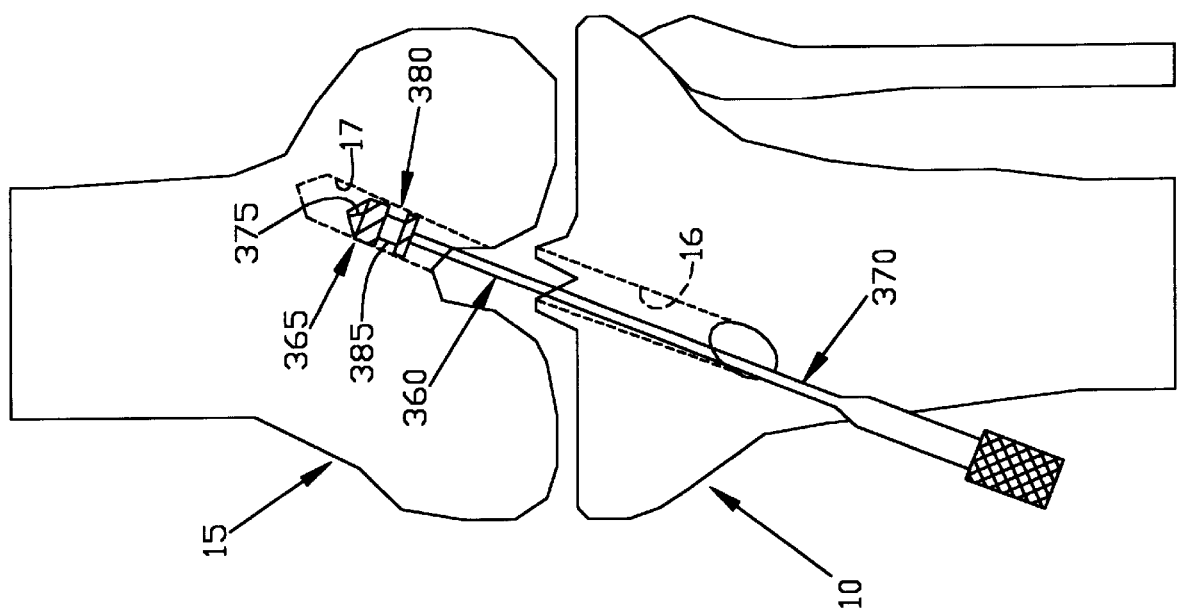

5,891,150

APPARATUS AND METHOD FOR FIXING A LIGAMENT IN A BONE TUNNEL

FIELD OF THE INVENTION

The present invention relates to surgical apparatus and methods in general, and more particularly to apparatus and methods for fixing a ligament in a bone tunnel.

BACKGROUND OF THE INVENTION

In the human knee, the anterior and posterior cruciate ligaments (i.e., the ACL and PCL) extend between the top end of the tibia and the bottom end of the femur. These ligaments play an important role in providing both static and dynamic stability to the knee. Often, the anterior cruciate ligament (i.e., the ACL) is ruptured or torn as a result of, for example, a sports-related injury. Consequently, various surgical procedures have been developed for reconstructing the ACL so as to restore stable function to the knee.

For example, the ACL may be reconstructed by replacing the ruptured ACL with a synthetic or harvested graft ligament. More particularly, with such procedures, bone tunnels are typically formed in the top end of the tibia and the bottom end of the femur, with one end of the graft ligament being positioned in the femoral tunnel and with the other end of the graft ligament being positioned in the tibial tunnel. The two ends of the graft ligament are anchored in place in various ways well known in the art so that the graft ligament extends between the tibia and the femur in substantially the same way, and with substantially the same function, as the original ACL.

In some circumstances, the graft ligament may include a bone block connected to one of its ends. This bone block may be used to attach the ligament graft to the patient's femur.

For example, in one well-known procedure, the bone block is placed in the femoral tunnel and then fixed in place using a so-called "Kurosaka" screw. More particularly, with this procedure, a screw is screwed into the bottom end of the femur so that the screw extends parallel to the bone tunnel and simultaneously engages both the bone block and the femur. This screw then keeps the bone block (and hence the graft ligament) secured to the femur.

More recently, interest has developed in procedures for pinning the bone block to the femur by passing a screw through the femur and the bone block so that the screw extends transverse to the bone tunnel. See, for example, U.S. Pat. Nos. 4,901,711; 4,985,032; 5,067,962; 5,152,764; 5,350,380; 5,354,300; 5,397,356; and 5,431,651.

Unfortunately, however, the various apparatus and methods disclosed in the foregoing patents suffer from a variety of deficiencies.

Furthermore, in some circumstances, the graft ligament may not have a bone block attached to one of its ends. In this situation, it can be difficult to securely attach the graft ACL to the patient's femur.

In this latter respect, some work has been done to pass a pin through the femur so that the pin extends transverse to the bone tunnel; the graft ACL is then looped over the pin to secure it to the femur. See, for example, U.S. Pat. Nos. 5,266,075 and 5,393,302.

Unfortunately, however, the various apparatus and methods disclosed in the foregoing patents also suffer from a variety of deficiencies.

Still other art of interest is shown in U.S. Pat. Nos. 3,973,277; 5,004,474; 5,147,362; 5,356,435; and 5,376,119.

OBJECTS OF THE INVENTION

Accordingly, one object of the present invention is to provide improved apparatus for fixing a ligament in a bone tunnel.

Another object of the present invention is to provide an improved method for fixing a ligament in a bone tunnel.

Still another object of the present invention is to provide improved apparatus for attaching a graft ACL to a patient's femur.

Yet another object of the present invention is to provide an improved method for attaching a graft ACL to a patient's femur.

SUMMARY OF THE INVENTION

These and other objects of the present invention are addressed by the provision and use of novel apparatus for fixing a ligament in a bone tunnel.

The novel apparatus comprises a novel drill guide assembly for forming transverse guide holes in a bone, and novel transverse screws for fixing a graft ligament in a bone tunnel.

In a preferred embodiment of the present invention, the drill guide assembly generally comprises a track member, a boom member, a stem member and a guide member. The track member has an elongated curved configuration. A bore extends through the track member at a first end thereof. A curved slide track extends inwardly from a second end of the track member. The boom member comprises a first portion and a second portion. The first portion has an elongated curved configuration which is adapted to be slidably disposed in the slide track of the track member. The second portion of the boom member has a planar configuration and includes a plurality of apertures extending therethrough for guiding drill bits or guidewires. The stem member comprises an elongated stem portion for extending through the bore in the track member and into the bone tunnel. The guide member is attached to the distal end of the stem portion, and has at least one recess therein for receiving distal ends of the drill bits received in the apertures of the boom member.

In accordance with a further feature of the present invention, there are provided transverse screws for fixing a ligament in a bone tunnel.

The transverse screws include a compression screw for compressing a bone plug against a wall portion of the bone tunnel, the compression screw having a concave distal end.

The transverse screws further include a transfixation screw for fixing the bone plug and/or its associated ligament to a wall portion of the bone tunnel, the transfixation screw having a pointed distal end for penetration of the bone plug and/or the ligament, and the bone tunnel wall.

The transverse screws still further include a combination transfixation and compression screw for compressing the bone plug against a wall portion of the tunnel and/or for fixing its associated ligament to the bone tunnel wall, the combination screw having, proximate a distal end thereof, a shoulder for engaging and pressing against the bone plug and/or the ligament, and a pin portion extending distally from the shoulder and pointed at the distal end thereof for penetration of the bone plug and/or the ligament, and the bone tunnel wall.

In accordance with a further feature of the present invention, there is provided a method for fixing a ligament in a bone tunnel, the method comprising the steps of: (i) drilling a tunnel in the bone, and providing a drill guide assembly comprising a track member having, at a first end thereof, a bore therethrough and having, extending inwardly thereof from a second end thereof, a slide track, the drill guide assembly further comprising a boom member having a first portion slidably disposed in the slide track of the track member and a second portion having an aperture therethrough, a stem member having an elongated stem portion, and a guide member having a recess therein, the guide member being fixed to the distal end of the stem member; (ii) positioning the stem member in the track member bore and the guide member at a selected location within the tunnel; (iii) placing a drill bit in the boom member's aperture, sliding the first portion of the boom member in the slide track of the track member so as to position the drill bit at a selected angle relative to the guide member, and locking the boom member to the track member; (iv) advancing the drill bit through the aperture in the boom member and into the recess of the guide member so as to form a transverse hole in the bone; (v) withdrawing the drill bit from the bone and withdrawing the stem member and the guide member from the tunnel; and (vi) fixing the ligament in the bone tunnel by means of a transverse screw extending through the transverse hole.

In one form of the invention, the graft ligament includes a bone block at its distal end which is made fast in the bone tunnel by passing a transverse screw through the transverse hole so that the transverse screw engages the graft ligament. In this situation, the guide member preferably comprises a guide plug having a recess therein for receiving the distal end of the drill bit.

In another form of the invention, the graft ligament does not include a bone block at its distal end, and the graft ligament is simply looped over a transverse element which is passed through the transverse hole and across the bone tunnel. In this situation, the guide member preferably comprises a guide yoke having two legs defining a gap therebetween.

BRIEF DESCRIPTION OF THE DRAWINGS

These and other objects, features and advantages of the present invention will be more fully disclosed in, or rendered obvious by, the following detailed description of the preferred embodiments of the invention, which is to be considered together with the accompanying drawings wherein like numbers refer to like parts, and further wherein:

FIG. 2 is a sectional view of a track member portion of the drill guide assembly;

FIG. 3 is a sectional view taken along line 3—3 of FIG. 2;

FIG. 14 is similar to FIG. 1, but illustrative of a use of the drill guide assembly in carrying out another embodiment of the inventive method;

FIG. 15 is similar to FIG. 7, but illustrative of an alternative embodiment of guide member;

FIG. 16 is a front elevational view of the stem member of FIG. 15;

FIGS. 17–21 are diagrammatic illustrations showing a sequence of steps in carrying out the alternative method referred to above in connection with FIG. 14;

FIG. 22 is similar to FIG. 2, but illustrative of an alternative embodiment of the track member portion of the drill guide assembly;

FIG. 23 is a sectional view taken along line 23—23 of FIG. 22;

FIG. 24 is similar to FIG. 4, but illustrative of an alternative embodiment of the boom member portion of the drill guide assembly;

FIG. 25 is an enlarged elevational view of a portion of the boom member of FIG. 24;

FIG. 26 is a sectional view taken along line 26—26 of FIG. 24;

FIG. 28 is a diagrammatic view illustrative of another alternative embodiment of the present invention.

DETAILED DESCRIPTION OF THE PREFERRED EMBODIMENTS

Figure 1:
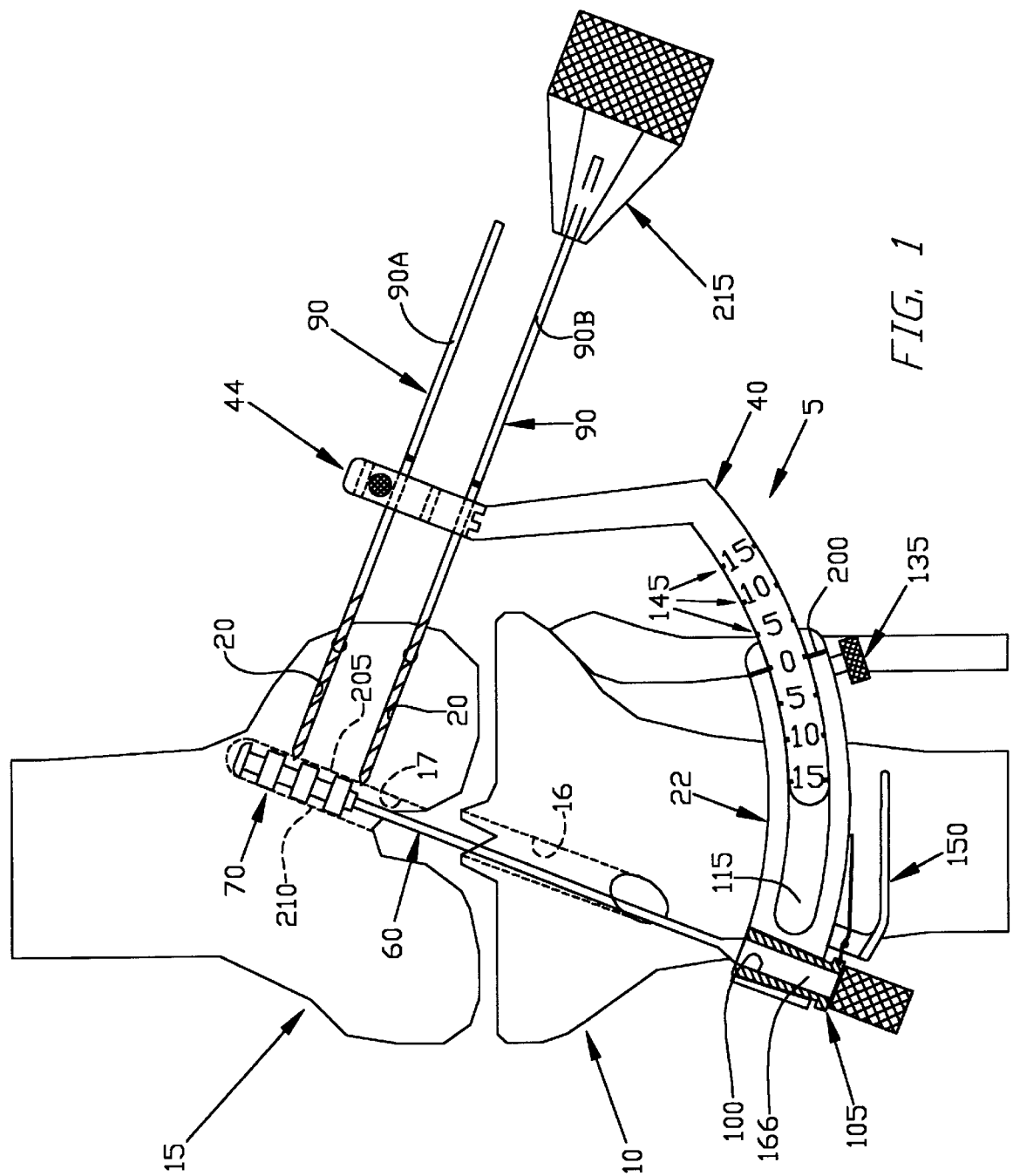
FIG. 1 is a side elevational view, partly sectional and partly diagrammatical, of one form of drill guide assembly formed in accordance with the present invention.

Referring first to FIG. 1, there is shown an illustrative embodiment of the inventive drill guide assembly 5, shown in conjunction with a tibia 10 and a femur 15 of a human knee joint. In substituting an artificial or harvested ligament for a damaged knee ligament, it is customary to drill a bone tunnel 16 through tibia 10 and another bone tunnel 17 into femur 15. A bone plug 18 (FIG. 8) having ligament material 19 fixed thereto is passed through the tibial tunnel 16 and into the femoral tunnel 17 for disposition within femoral tunnel 17. The drill guide assembly 5 shown in FIG. 1 is intended to be used to drill transverse holes 20 into femur 15. These transverse holes 20 receive transverse screws 21 (FIG. 8) so as to secure bone plug 18 in femur 15.

The drill guide assembly 5 includes a track member 22, a boom member 40, a stem member 60, and a guide plug 70 connected to the distal end of stem member 60. The boom member 40 includes a portion 44 adapted to receive drill bits 90 for drilling the transverse holes 20. As mentioned above, the transverse holes 20 are thereafter adapted to receive transverse screws 21 (FIG. 8) for securing bone plug 18 in femoral tunnel 17.

Referring next to FIGS. 2 and 3, it will be seen that the track member 22 has an elongated curved configuration. Track member 22 includes a first end 95. A bore 100 extends through track member 22 adjacent to first end 95. Bore 100 has a tapered configuration, such that its distal end (i.e., the end disposed closer to femur 15) is larger than its proximal end (i.e., the end disposed farther from femur 15). A slot 103 extends along the length of bore 100. A collet 105 is disposed in bore 100. Collet 105 also has a tapered configuration, such that its distal end (i.e., the end disposed closer to femur 15) is larger than its proximal end (i.e., the end disposed farther from femur 15). A slot 108 extends along the length of collet 105. The collet's slot 108 is aligned with the track member's slot 103, for reasons which will hereinafter be made clear. Collet 105 is formed out of a resilient material, e.g., plastic or metal. Track member 22 also includes a second end 110. A curved slide track 115 extends inwardly from second end 110. The curvature of slide track 115 conforms to the curvature of track member 22.

Figure 4:
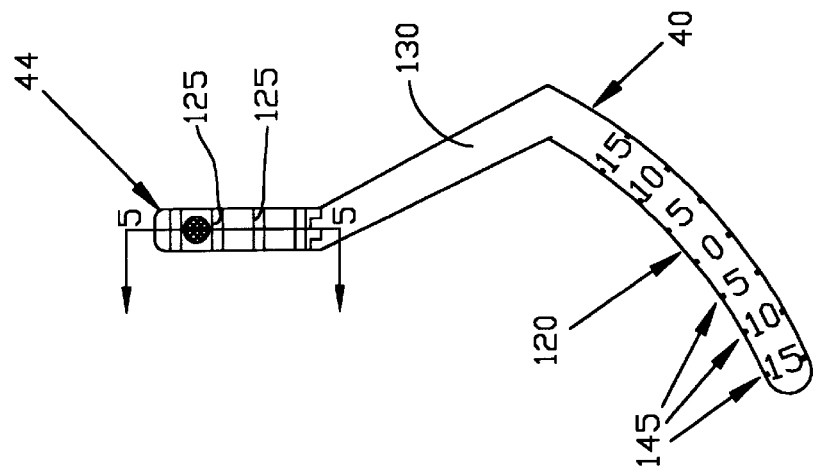
FIG. 4 is a side elevational view of a boom member portion of the drill guide assembly.

In FIG. 4, there is shown boom member 40. Boom member 40 has a first portion 120 of an elongated curved configuration which is complementary to slide track 115 in track member 22 so that the boom member's first portion 120 can be slidably disposed in slide track 115 (FIG. 1). The boom member 40 also includes the second portion 44 which has a substantially planar configuration. The second portion 44 of boom member 40 is provided with a plurality of apertures 125 therethrough. An intermediate portion 130 interconnects the boom member's first portion 120 and second portion 44.

A thumbscrew 135 (FIGS. 1–3) is mounted in track member 22 and is adapted to lock the boom member's first portion 120 in a selected position in slide track 115 by manipulation of a grip portion 140. Manipulation of grip portion 140 releases the boom member's first portion 120 for movement in slide track 115. Preferably, the boom member's first portion 120 is provided with indicia 145 (FIGS. 1 and 4) indicative of the angular positioning of boom member 40 in track member 22, as will be further discussed hereinbelow.

The track member 22 has a handle 150 (FIGS. 1 and 2) and a spring 165 mounted thereon. One end of spring 165 engages the proximal end of collet 105 and the other end of spring 165 engages track member 22, whereby spring 165 normally biases collet 105 proximally in bore 100. However, handle 150 is arranged so that when it is moved towards track member 22, spring 165 will move collet 105 distally within bore 100. In this respect it is to be appreciated that, by virtue of the tapered configurations of bore 100 and collet 105, and by virtue of the collet's resilient nature and its slot 108, collet 105 will be in a "closed down" position when it is moved proximally within bore 100 by spring 165, and collet 105 will be in an "opened up" position when it is moved distally within bore 100 by handle 150. Furthermore, it is to be appreciated that when stem member 60 is disposed within collet member 105 (FIG. 1), collet member 105 will normally tightly grip the stem member's enlarged proximal portion 166, due to the biasing action of spring 165, but collet member 105 can be induced to release its grip on stem member 60 by depressing handle 150.

It should also be appreciated that the arrangement of bore 100, collet 105, handle 150 and spring 165 is generally similar to the corresponding arrangement taught in U.S. Pat. No. 5,154,720 issued Oct. 13, 1992 to Trott et al., which patent is hereby incorporated herein by reference.

Figure 5:
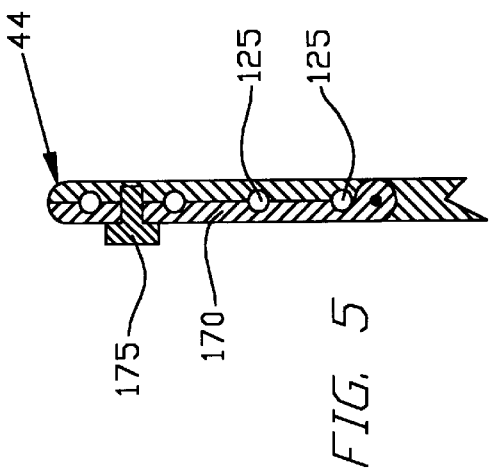
FIG. 5 is a sectional view taken along line 5—5 of FIG. 4.
Figure 6:
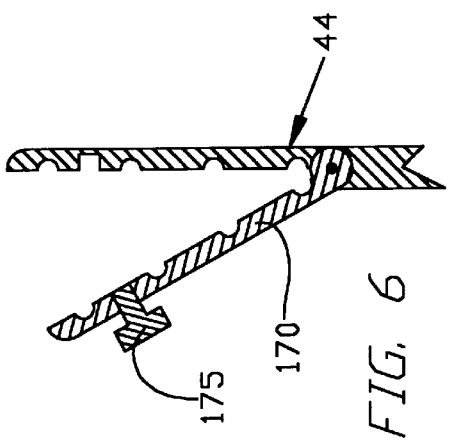
FIG. 6 is similar to FIG. 5, but shows components in different positions.

Referring next to FIGS. 5 and 6, it will be seen that the boom member's second portion 44 includes a pivotally mounted plate 170 secured to, and released from, second portion 44 by a thumbscrew 175. By manipulation of thumbscrew 175, plate 170 may be released from, and pivotally moved outwardly from, second portion 44 (FIG. 6) so as to permit drill bits 90 to be laterally released from apertures 125. This feature is very useful in the situation where the drill guide assembly 5 must be removed from the surgical site while the drill bits 90 (or guidewire 305, as will hereinafter be discussed) remain embedded in the femur.

Figure 7:
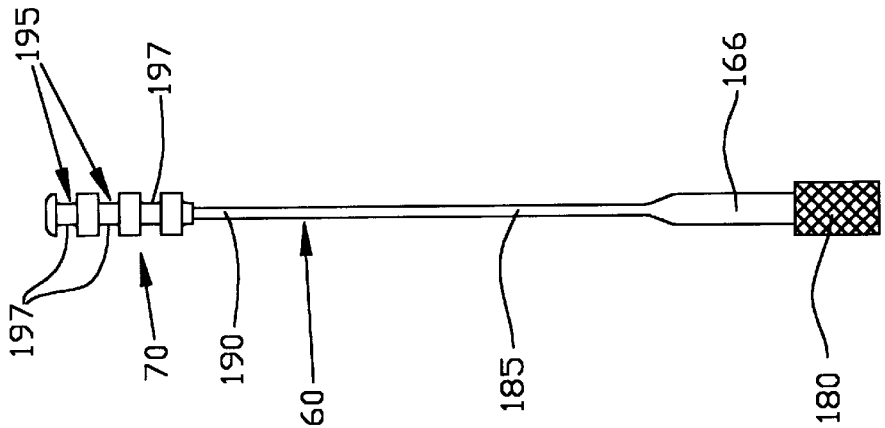
FIG. 7 is a side elevational view of stem member and guide plug portions of the drill guide assembly.

Referring next to FIG. 7, it will be seen that the stem member 60 includes a handle portion 180 adjacent to the enlarged proximal portion 166, and an elongated stem portion 185. The elongated stem portion 185 is sized so as to be slightly thinner than the width of the track member's slot 103, and slightly thinner than the width of the collet's slot 108 when the collet has been moved distally by means of handle 150, whereby the elongated stem portion 185 can be passed through the slots. The elongated stem portion 185 is connectable, at a distal end 190 thereof, to the guide plug 70. Guide plug 70 has a series of recesses 195 therein, preferably in the form of annular grooves 197 encircling guide plug 70.

As shown in FIG. 1, the track member's bore 100 receives collet 105 and collet 105 receives stem member 60, with guide plug 70 fixed thereon. Stem member 60 can gain access to the interior of collet 105 by (i) depressing handle 150 so as to move collet 105 distally whereby it will open its slot 108, and (ii) slipping the stem member's reduced-diameter stem portion 185 through the aligned slots 103 and 108. It will be appreciated that stem member 60 can exit the interior of collet 105 by reversing the foregoing procedure.

The stem member 60 is intended to be inserted axially into tibial tunnel 16 and then femoral tunnel 17 until guide plug 70 occupies the position in which bone plug 18 ultimately will be disposed. When guide plug 70 is correctly positioned in femoral tunnel 17, handle 150 can be released so that collet 105 will move proximally until it securely grips the guide member's enlarged proximal portion 166. The annular grooves 197 on guide plug 70 will be correctly aligned with the apertures 125 of the boom member's second portion 44 when the handle portion 180 stem member 60 is seated on the proximal surface of collet 105. The guide plug 70 is of a slightly lesser diameter than femoral tunnel 17. The thumbscrew 135 is manipulated by an operator to permit sliding movement of the boom's first portion 120 in slide track 115 of track member 22. If it is desired that transverse screws 21 be brought to bear on the bone plug and/or ligament at right angles to the axis of the femoral tunnel 17, thumbscrew 135 is fixed when the marking "0" on the boom's first portion 120 is aligned with a base mark 200 on track member 22, as illustrated in FIG. 1.

The intermediate portion 130 (FIG. 4) of boom member 40 inclines from the boom member's first portion 120 toward stem member 60 so as to place the boom member's second portion 44 closer to guide plug 70 than would be the case if intermediate portion 130 were merely an extension of first portion 120. The incline of intermediate portion 130 places second portion 44 in a position proximate to, and opposed to, guide plug 70, as shown in FIG. 1. With track member 22 and boom member 40 locked together with the base mark 200 at the setting "0", the boom member's second portion 44 is disposed parallel to guide plug 70 and its apertures 125 are disposed normal to the axis of guide plug 70 and in alignment with the guide plug's annular grooves 197. In particular, at this drill guide setting, each of the apertures 125 is in alignment with one of the annular grooves 197.

The apertures 125 are adapted to receive drill bits 90 of a length sufficient to extend through the nearest wall portion 205 and the farthest wall portion 210. Markings 91 on drill bits 90 are used to indicate the depth to which the drill bits 90 have penetrated. Each of the drill bits 90 is adapted to be secured to a chuck 215 (FIG. 1) of a drill (not shown) for drilling operations. Drill bits 90 are provided in varying lengths so that a first (i.e., shorter) drill bit 90A can be left positioned in the femur while a second (i.e., longer) drill bit 90B is drilled in close to the first drill bit 90A; the increased length of the second drill bit 90B allows it to be driven into the femur without the drill's chuck striking the already-emplaced first drill bit 90A.

Alternatively, apertures 125 can be adapted to receive bushings (not shown) having holes dimensioned, respectively, to receive tools such as drill bits, guide wires, and the like. In such case, the boom member's second portion 44 is provided with means of the sort well known in the art (not shown) for locking the bushings in the apertures 125.

If desired, the boom member's second portion 44 can also be provided with locking means of the sort well known in the art (not shown) such as thumbscrews for locking the tools in the apertures 125.

Figure 9:
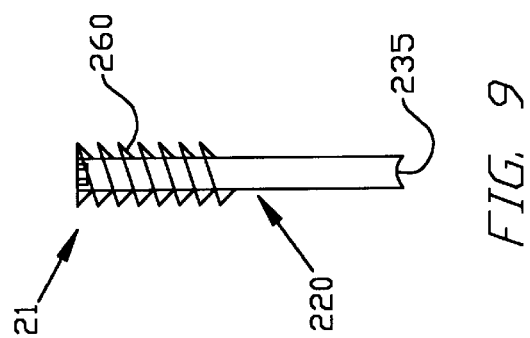
FIGS. 9 and 10 are side elevational views of forms of transverse screws, illustrative of embodiments of further components of the present invention.
Figure 10:
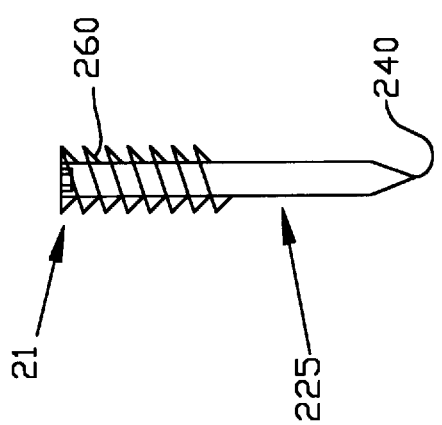
Figure 12:
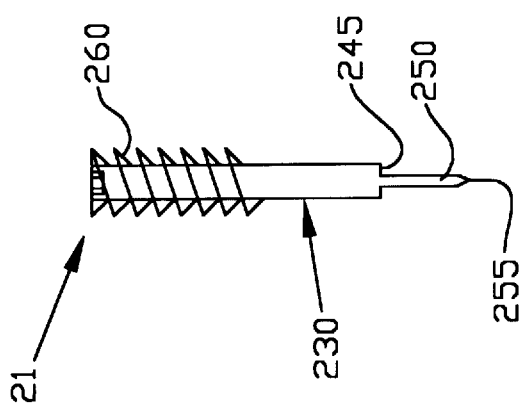
FIG. 12 is similar to FIGS. 9 and 10, but illustrative of an alternative embodiment of transverse screw.

In FIGS. 9, 10 and 12, there are shown various embodiments of transverse screws 21, including a compression screw 220 (FIG. 9), a transfixation screw 225 (FIG. 10) and a combination transfixation and compression screw 230 (FIG. 12).

Figure 8:
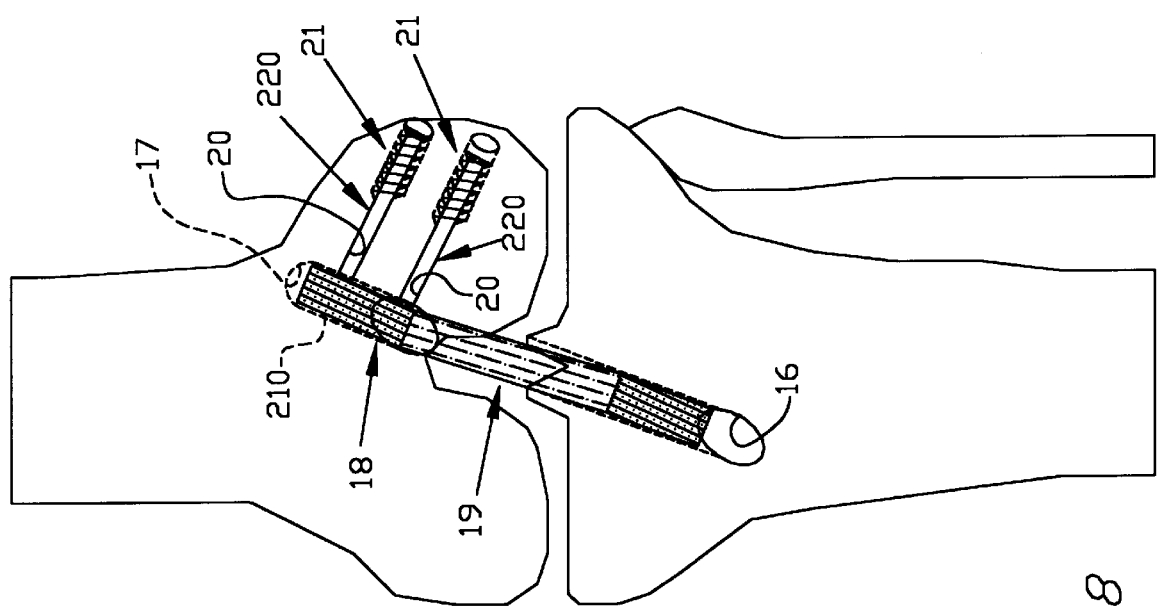
FIG. 8 is similar to FIG. 1, but with the drill guide assembly removed and with transverse screws inserted in transverse drill holes.

The compression screw 220 is provided with a concave distal end 235. The compression screw 220 is used for compressing the bone plug 18 against the farthest femoral tunnel wall portion 210, as shown in FIG. 8. Typically, the bone plug wall facing the screw's concave distal end 235 is of relatively hard cortical bone, and the bone plug wall facing the tunnel wall portion 210 is of relatively soft cancellous bone. This permits the cancellous portion of the bone plug to be pressed into close engagement with the femur's tunnel wall portion 210, whereupon the portions of bone may thereafter grow together.

Figure 11:
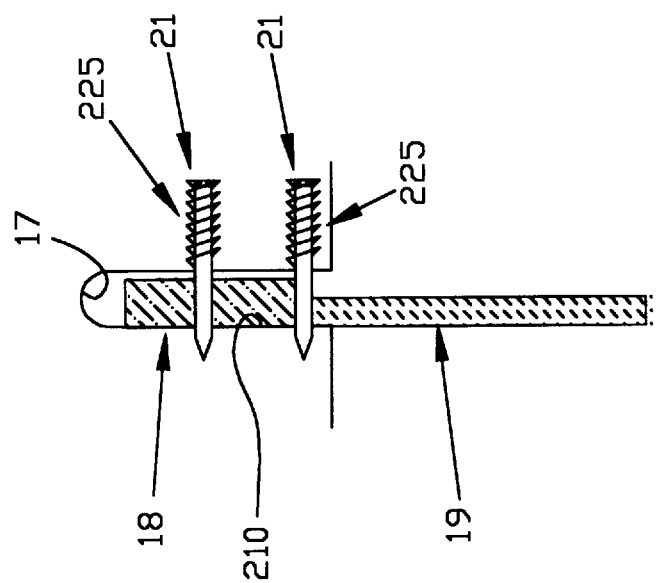
FIG. 11 is a diagrammatic representation showing screws of the type shown in FIG. 10 in place in a bone tunnel.

The transfixation screw 225 (FIGS. 10 and 11) is provided with a pointed distal end 240 for penetration of bone plug 18 and/or ligament material 19, and farthest wall portion 210 of femoral tunnel 17. In FIG. 11, there are shown two transverse screws 21 of the transfixation type 225, one shown extending through the bone plug 18 and into the farthest wall 210, and a second shown extending through ligament material 19 and into the farthest wall 210.

The compression screws 220 and transfixation screws 225 may be used in various combinations. For example, one or more of the compression screws 220 may be used to secure bone plug 18, as shown in FIG. 8, and one or more of the transfixation screws 225 may be used to support bone plug 18 and/or ligament material 19, and/or to act as stop members for bone plug 18, as shown in FIG. 11.

Figure 13:
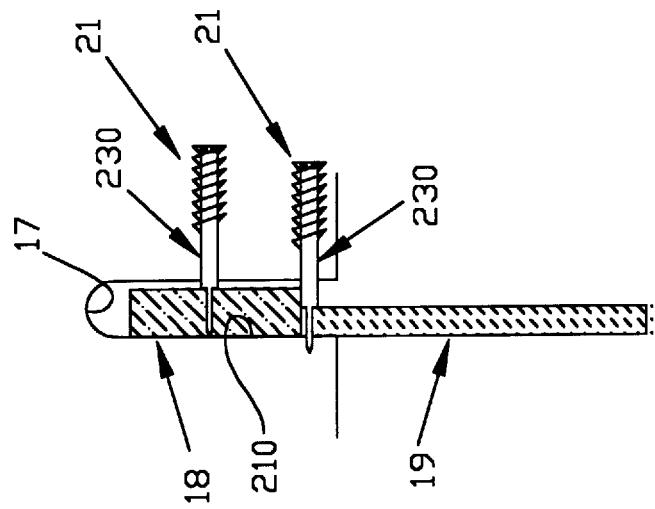
FIG. 13 is similar to FIG. 11, but illustrative of screws of the type shown in FIG. 12 in place in a bone tunnel.

Referring next to FIG. 12, it will be seen that the combination transfixation and compression screw 230 is provided, proximate the distal end thereof, with (i) a shoulder 245 for engaging and pressing against bone plug 18 and ligament material 19, and (ii) a pin portion 250 extending distally from shoulder 245 and pointed at a distal end 255 for penetration of bone plug 18 and/or ligament material 19, and farthest wall 210. As shown in FIG. 13, one or more of the combination screws 230 may be used such that pin portion 250 extends into bone plug 18 and shoulder 245 engages and presses against bone plug 18, and one or more of the combination screws 230 may be used such that shoulder 245 presses against ligament material 19 while pin portion 250 extends through the ligament material 19 and into farthest wall 210 of femoral tunnel 17. In the embodiment shown in FIG. 13, the ligament-engaging combination screw 230A (i.e., the proximal-most screw 230) may be deployed first and the bone plug 18 then pulled down against the screw, whereupon the distal-most combination screw 230B (as shown in FIG. 13) may be advanced into bone plug 18 so as to secure the bone plug in femoral tunnel 17 by transfixing and compressing bone plug 18 against farthest wall portion 210. In such an arrangement, the proximal-most screw 230A serves to pin ligament material 19 against tunnel wall 210 and further serves as a stop member and support member for bone plug 18.

The transverse screws 21 are each provided with screw threads 260 near the proximal end thereof, and are not threaded near the distal end of the screw. The threads 260 thus facilitate securely locking transverse screws 21 in holes 20, but do not engage bone plug 18 or ligament material 19, and therefore do not threaten the integrity of the bone plug and the associated ligament material. Transverse screws 21 are headless, so that they may be buried in femur 15 and not protrude above the outer surface of the femur. Additionally, since transverse screws 21 are headless, they may be advanced however far into femur 15 as may be required to achieve the degree of graft penetration or compression desired.

In operation, the drill guide assembly 5 is positioned relative to the knee joint as shown in FIG. 1, track member 22 and boom member 40 being locked together in a selected relationship to place apertures 125 at a desired angle relative to guide plug 70. Drill bits 90 are then used to drill guide holes 20. For example, where two guide holes 20 are intended to be drilled into the femur, and where these drill bits may or may not be left in the femur for some period of time after drilling, a shorter drill bit 90A and a longer drill bit 90B would be used. First the shorter drill bit 90A is drilled into the bone. When this occurs, one of the annular grooves 197 of guide plug 70 receives the pointed end of drill bit 90A so that a guide hole 20 is fully formed from the entry point on femur 15 into the femoral tunnel 17. Then the longer drill bit 90B is used to drill an additional hole 20. Since drill bit 90B is longer than the already-deployed drill bit 90A, the drill bit 90B can be placed close to drill bit 90A without the chuck of the drill striking the emplaced drill bit 90A. Drill bits 90 are withdrawn and the drill guide assembly removed, and bone plug 18 is then installed in femoral tunnel 17 using techniques well known in the art.

Transverse screws 21 are then screwed into guide holes 20 so as to engage bone plug 18 and/or ligament material 19 in the manner previously discussed. Transverse screws 21 will thus secure bone plug 18 and ligament material 19 in femoral tunnel 17. The transverse screws 21 are headless so as to permit the screws to be buried completely in femur 15. In addition, since the transverse screws 21 are headless, they can be advanced as far into femur 15 as may be required to achieve the degree of graft penetration or compression desired.

Certain aspects of drill guide assembly 5 should be noted.

For one thing, it should be appreciated that the central longitudinal axis of the stem member 60 and the central longitudinal axes of the apertures 125 are disposed in the same plane.

Furthermore, the longitudinal axis of the stem member 60 will intersect, when stem member 60 is properly seated within collet 105, the longitudinal axes of the apertures 125. By the same token, drills or guidewires advanced through the apertures 125 with a sliding fit will intersect the longitudinal axis of the stem member 60 and, in particular, recesses 195 in guide plug 70.

In addition to the foregoing, it should be appreciated that the axis of rotation for track member 22 intersects the longitudinal axis of the stem member 60. This axis of rotation is oriented perpendicular to the plane defined by the longitudinal axis of the stem member 60 and the longitudinal axes of the apertures 125. The axis of curvature for track member 22 (and the point of intersection between the longitudinal axis of stem member 60 and the longitudinal axes of apertures 125) is preferably located within the guide plug 70.

FIG. 14 is illustrative of an alternative procedure in which the inventive drill guide finds applicability. In the procedure illustrated, the guide plug 70 is replaced with a guide yoke 270 (FIGS. 15 and 16) having a base portion 275 and two elongated substantially parallel legs 280 extending therefrom and defining therebetween a gap 285 (FIG. 16). Each leg 280 is provided with a notch 290 (FIG. 15) on its distal end. The guide member's handle portion 180 includes an orientation mark 292 which has a predefined orientation relative to guide yoke 270 whereby, when guide yoke 270 is disposed within femoral tunnel 17, the orientation of guide yoke 270 can be determined by observing the position of orientation mark 292. Preferably orientation mark 292 is arranged so that when orientation mark 292 is aligned with slot 103 in track member 22 and slot 108 in collet 105, the guide yoke's gap 285 will be aligned with a drill bit in the boom member's apertures 125. If desired, orientation mark 292 can be replaced with equivalent mechanical means of the sort well known in the art (not shown) for enabling alignment of the guide yoke's gap 285.

The object of the procedure illustrated in FIG. 14 is to suspend a ligament 295 over a cross-pin in the femoral tunnel 17, where the ligament 295 does not have a bone plug on its end. To do so, the ligament 295 is attached at one end to an end of a suture 300, or the like. The suture 300 is strung through the guide yoke's leg notches 290, bridging the gap 285 proximate the distal end of guide yoke 270. The suture 300 is passed into femoral tunnel 17 by movement of guide yoke 270 through tibial tunnel 16 and into femoral tunnel 17. With the enlarged proximal portion 166 of stem member 60 positioned within collet 105, and with handle 150 depressed so as to permit the stem member's enlarged proximal portion 166 to move within the collet, the handle portion 180 of stem member 60 is rotated until the orientation mark 292 is aligned with slot 103 in track member 22 and slot 108 in collet 105. In this position, the guide yoke's gap 285 will be aligned with the apertures 125 of second portion 44. The stem member 60 is then locked in place by releasing the handle portion 150 of track member 22. As shown in FIG. 14, at this point the two ends of suture 300 extend from the tibial tunnel 16, with ligament 295 fixed to one of the two ends.

When guide yoke 270 is properly positioned in femoral tunnel 17, a drill bit 90 (mounted in one of the apertures 125 of second portion 44 of boom member 40) is drilled into femur 15, using the above-described drill guide for proper alignment of drill bit 90 with guide yoke 270. The drill guide directs drill bit 90 through guide yoke gap 285. The drill bit 90 continues into farthest femoral tunnel wall portion 210. The drill bit 90 is then withdrawn and the guidewire 305 is inserted into the hole 20 created by the drill bit 90, and drilled or tapped further into the femoral tunnel wall portion 210 than was the drill bit 90 (FIG. 17).

Alternatively, the use of drill bit 90 can be omitted, and the drill guide assembly can be used to drill or tap guidewire 305 directly into place in femur 15.

With the guidewire 305 securely in place in the guide yoke gap 285, the guide yoke 270 is withdrawn from the femoral tunnel 17. This is done by depressing handle 150 so as to free stem member 60 from collet 105, and then withdrawing the stem member proximally. As the guide yoke 270 moves toward the tibia 10, suture 300 remains looped around guidewire 305, and leaves the notches 290 (FIG. 18). The stem member 60 may then be removed from the drill guide by slipping the elongated stem portion through the collet's slot 108 and the track member's slot 103.

By pulling the free end of suture 300, the operator may then pull ligament 295 through tibial tunnel 16 and up into femoral tunnel 17 (FIG. 19). Further pulling on the free end of suture 300 will pull ligament 295 up around guidewire 305 (FIG. 20) and then back down to the lower opening of tibial tunnel 16, where the two free ends of ligament 295 may be positioned for attachment to tibia 10 in ways well known in the art (not shown).

A cannulated transverse screw 310 (FIG. 20) is then advanced on the guidewire 305 and into hole 20 (FIG. 20). Transverse screw 310 is then advanced further, so that it passes through the looped ligament 295 (FIG. 21) and into femoral tunnel wall portion 210. Once the screw 310 is securely in place, the guidewire 305 may be removed from inside the screw 310 (FIG. 21) and withdrawn from femur 15, leaving ligament 295 looped around transverse screw 310. In order to facilitate passage of transverse screw 310 through the loop of ligament 295 resting on guidewire 305, the distal end of screw 310 is inclined at 315 (FIG. 20) and has a smooth outer configuration along a first portion 320 of its shaft. A second portion 325 of its shaft is threaded so as to facilitate securely locking the transverse screw 310 in hole 20.

In FIGS. 22 and 23, there is shown an alternative embodiment of track member 22A, wherein there is provided a thumb screw 330 engageable with collet 335 and adapted to squeeze collet 335, by tightening down of thumb screw 330, to lock stem member 60 therein. Loosening of thumb screw 330 releases pressure on collet 335 to permit expansion of collet 335, which is a split collet (FIG. 23), to loosen the stem member 60 for backing stem member 60 out of collet 335. It is to be appreciated that collet 335 (like collet 105 described above) is not large enough to permit passage of guide plug 70 therethrough. Upon the guide plug 70 encountering collet 335, aligned slots 340, 345 in collet 335 and track member 22A, respectively, permit sidewise movement of the elongated stem portion 185 of stem member 60 from the confines of collet 335.

It is to be appreciated that the track member 22 and collet 105 of FIG. 2 have the same sidewise escape feature (i.e., slot 108 in collet 105 and slot 103 in track member 22). However, in the embodiment shown in FIG. 2, the handle 150 serves to longitudinally move the collet 105 to the point where it releases its grip on stem member 60, and in the embodiment shown in FIG. 22, the thumbscrew 330 serves to loosen the collet 335 such that it no longer binds the stem member 60.

It is also to be appreciated that, after creating the transverse drill holes 20 as illustrated in FIGS. 1 and 14, the unique design of drill guide assembly 5 allows it to be quickly and easily detached from the drills 90 (and/or guidewire 305) and stem member 60 while leaving the drills 90 (and/or guidewire 305) and stem member 60 in-situ. The stem member 60 is released from the grip of the collet 105 by depressing the handle portion 150 of track member 22. Then, by sidewise movement of the slender portion 185 of stem member 60 past the aligned slots 108 and 103 in collet 105 and track member 22, respectively, the stem member 60 escapes from the confines of the drill guide assembly 5. Furthermore, by unlocking movement of thumbscrew 175, plate 170 may be released from, and pivotally moved outwardly from, the drill guide's second portion 44 (FIG. 6) so as to allow quick release of drill bits 90 (and/or guidewire 305) from apertures 125. The disengagement of the drills 90 (and/or guidewire 305), and stem member 60, from the drill guide assembly 5 can be further facilitated by unlocking movement of thumbscrew 135 to allow the first portion 120 of boom member 40 to slide along slide track 115 in track member 22.

FIGS. 24–26 show an alternative boom member 40A. In this construction, intermediate portion 130A slidingly supports a tray portion 342 of boom member second portion 44A, such that portion 44A may be slid toward or away from guide plug 70 (or guide yoke 270). The tray portion 342 is provided with recesses 345 into which a spring-biased detent 350 of the intermediate portion 130A may releasably snap-lock, or tray portion 342 may be provided with any other suitable releasable locking device for locking tray portion 342 in a selected position on intermediate portion 130A.

There is thus provided a drill guide assembly wherein transverse hole drilling bits may be operated at a selected angle to the axis of the bone tunnel. There is further provided a drill guide assembly wherein a plurality of hole drilling bits may be employed to provide a plurality of transverse holes intercepting the bone tunnel, such that transverse screws (selected from different types of transverse screws) may be disposed in the holes to penetrate and/or impinge upon and/or pass through a bone plug and/or associated ligament material and/or sutures, in different locations, to effect different modes of holding. There are still further provided methods for forming tunnels in bones and for fixing bone plugs and ligaments in such tunnels.

While access to the femoral tunnel 17 has been described hereinabove as being obtained via the tunnel 16 extending through the tibia 10, and while such is a common undertaking, such is not necessary in practicing the inventive methods herein described nor for use of the inventive drill guide and/or transverse screws. For example, as illustrated in FIG. 27, the skin near the upper plateau of the tibia may be opened at 355, whereby the guide plug 70 (and/or the guide yoke 270) may be introduced into femoral tunnel 17.

Figure 27:
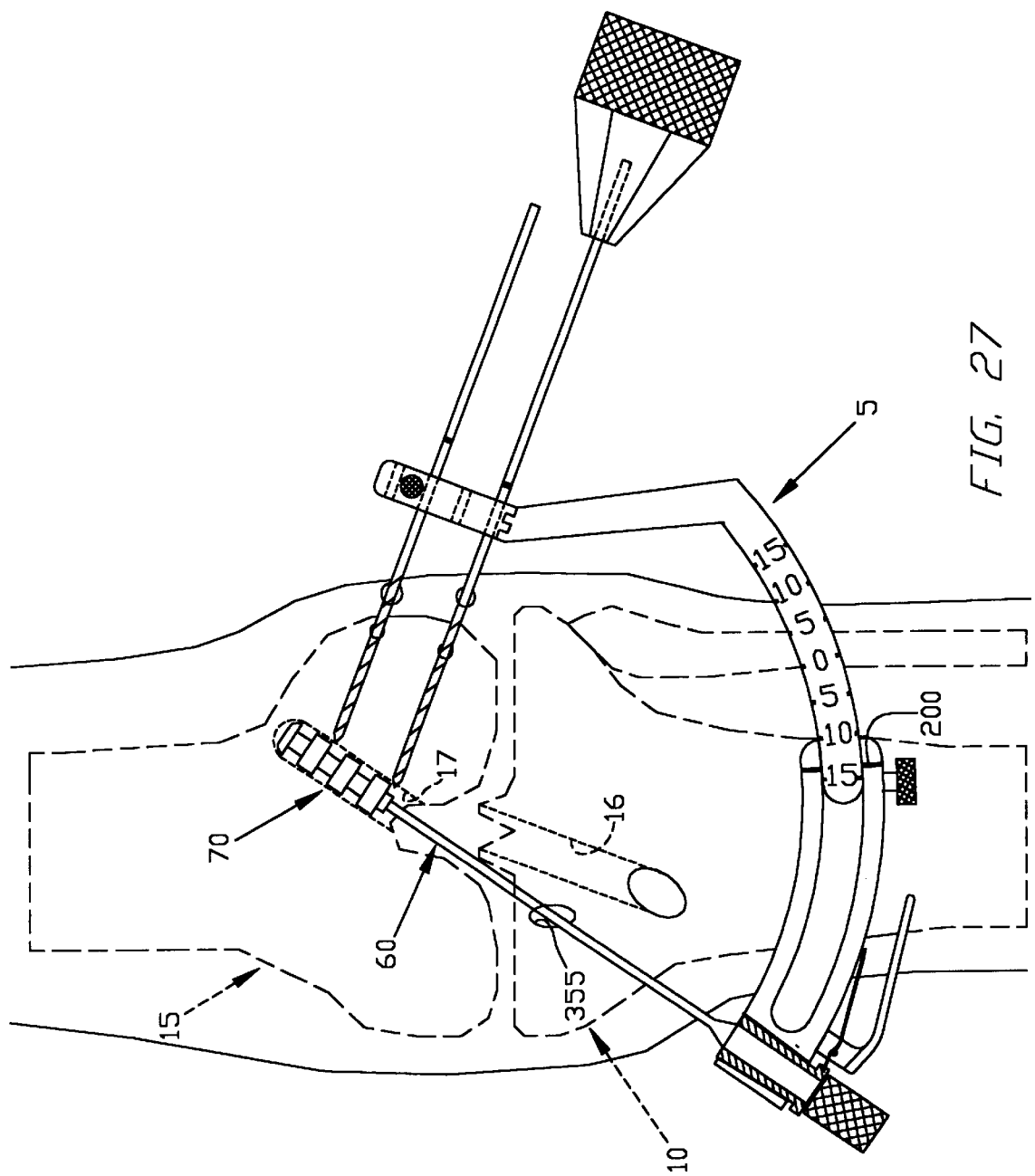
FIG. 27 is similar to FIG. 1, but shows the drill guide assembly in use in an alternative embodiment of the inventive method.

It is also to be appreciated that, as shown in FIG. 27, tibial tunnel 16 and femoral tunnel 17 need not necessarily be co-linear with one another. In fact, in some circumstances, tibial tunnel 16 and femoral tunnel 17 can be significantly divergent (i.e., non-co-linear).

Furthermore, in this respect, it should be appreciated that the unique construction of drill guide assembly 5 permits the surgeon significant freedom in selecting the optimal angles of approach when cross-pinning a graft ligament in femur 15. For example, in FIG. 27, a skin incision 355 may be used to form and gain access to a femoral tunnel 17 (which is not aligned with tibial tunnel 16) in the course of cross-pinning a graft ligament in femur 15. It should be noted that, in the exemplary case shown in FIG. 27, base mark 200 on track member 22 is aligned with the marking "15" rather than with the marking "0" as previously shown in FIG. 1.

Referring next to FIG. 28, there is shown a novel drill bit 360 having particular utility in connection with fixing a bone plug in a bone in the vicinity of a joint as, for example, fixing a bone plug in the femur in the vicinity of the knee joint. Drill bit 360 includes a head portion 365 and a stem portion 370. The head portion 365 is provided with bore cutting means 375, such as the usual cutting teeth extending generally helically around the drill head. The stem portion 370 is of a widthwise dimension substantially less than the diameter of head portion 365. Such drill bits are sometimes referred to as "acorn bits". After the head portion 365 advances through the tibia 10, there is defined in the tibia the tibial tunnel 16, which is generally of the same diameter as head portion 365. However, in view of the slender configuration of stem portion 370, the stem portion 370 may be moved about in tibial tunnel 16 as needed so as to place the drill bit head portion 365 at an appropriate entry point on the femur 15. Thus, tibial tunnel 16 and femoral tunnel 17 need not be in precise alignment with one another, affording a degree of flexibility in positioning of the tibia 10 and femur 15, and in the disposition of tibial tunnel 16 relative to femoral tunnel 17.

The drill bit head portion 365 may be provided with recesses 380 serving the same purpose as recesses 195 of guide plug 70. For example, recesses 380 might comprise annular grooves 385 similar to the annular grooves 197 in guide plug 70. In such instance, the head portion 365 can serve not only as a drill head, but also as a guide plug.

In an alternative method, utilizing the aforementioned "acorn bit" 360 in the knee joint, head portion 365 of bit 360 is advanced through tibia 10 to define bone tunnel 16 therethrough. The tibia 10 and femur 15 are then positioned for desired placement of bone tunnel 17 in femur 15. The drill bit 360 is angled (FIG. 28) in tibial tunnel 16 for placement of drill bit head portion 365 on femur 15 at a selected entry point for femoral tunnel 17, and drill bit 360 is advanced into femur 15 at the selected entry point. A drill guide assembly 5, such as described above, or similar thereto, is provided, and one or more transverse drill bits 90 in the drill guide are advanced through femur 15 to define transverse holes 20 extending into femoral tunnel 17. The transverse drill bits 90 are withdrawn and the femoral tunnel 17 is vacated. The bone plug 18 is then placed in the femoral tunnel 17 and transverse screws 21 are advanced through transverse holes 20 to engage bone plug 18 to secure bone plug 18 in femur 15.

In one embodiment of the method described immediately above, drill bit head portion 365 is provided with one or more recesses 380 and the transverse drill bits 90 are advanced into the recesses 380. With this embodiment of the invention, a separate guide plug 70 (having one or more of the recesses 195 therein) does not have to be provided. In another embodiment of the invention, there is provided the guide plug 70 having one or more of the recesses 195 therein. In this latter embodiment, the drill bit head portion 365 is removed from femoral tunnel 17 prior to advancement of the transverse drill bits 90. More particularly, with this latter embodiment of the invention, the drill bit head portion 365 is removed from the femoral tunnel 17 after the femoral tunnel has been formed, next the guide plug 70 is inserted into the femoral tunnel 17, and then the transverse drill bits 90 are advanced into the guide plug recesses 195.

It should be understood that various modifications, variations and changes may be made to the above-disclosed novel drill guide assembly, transverse screws and drill bit, and the above-described methods, without departing from the spirit and scope of the present invention. For example, while the above-described devices and methods have been described and shown with respect to a femur-tibia joint, and while the aforesaid devices and methods are believed to have particularly beneficial applicability to such joints, it will be appreciated that the devices described herein find utility with respect to bones generally and should not be deemed limited to simply the femur and tibia bones. Further, when two bones are involved, it is clear that the near (i.e., proximal) tunnel can be made in either bone (e.g., the femur), that the drill guide device can be used in any attitude as, for example, upside-down from the arrangement shown in FIG. 1, and that bone plugs can be secured in both bones following the teachings of the present invention. It will further be appreciated that the methods described herein have been limited to the inventive steps of the methods and have omitted many surgical steps required and well-known in the art, from initiating stab wounds in the skin proximate selected bone entry points so as to make such points accessible, to suturing such incisions at the conclusion of the operation.

What is claimed is:

1. A drill guide assembly for forming a transverse guide hole in a bone, the guide hole being adapted to receive a transverse element, the guide hole intersecting a tunnel formed in the bone and adapted to receive a body to be retained in said tunnel and adapted to receive the transverse element to lock the body in the tunnel, said drill guide assembly comprising:

a track member of an elongated curved configuration, said track member having a bore extending widthwise thereof and a curved slide track extending lengthwise thereof;

a boom member having a first portion of an elongated curved configuration slidably disposed in said slide track of said track member, and a second portion for retaining a drill implement;

a stem member for disposition in said track member bore, said stem member having an elongated stem portion for extending into the tunnel; and a guide member for attachment to a distal end of said stem portion, said guide member having a recess therein for receiving a distal end of a drill implement retained in said second portion of said boom member.

2. A drill guide assembly for forming transverse guide holes in a bone, the guide holes being adapted to receive transverse screws, the guide holes intersecting a tunnel formed in the bone and adapted to receive a bone plug and to receive the screws transversely of the bone plug to secure the bone plug in the tunnel, said drill guide assembly comprising:

a track member of an elongated curved configuration, said track member having at a first end thereof a bore therethrough and having extending inwardly thereof from a second end thereof a curved slide track;

a boom member having a first portion of an elongated curved configuration slidably disposed in said slide track of said track member, and a second portion adapted for retaining drill bits;

a stem member for disposition in said track member bore, said stem member having an elongated stem portion for extending into the tunnel; and a guide plug for attachment to a distal end of said stem portion, said guide plug having recesses therein for receiving distal ends of the drill bits retained in said apertures.

3. A drill guide assembly according to claim 2 further comprising means for releasably locking together said track member and said first portion of said boom member.

4. A drill guide assembly according to claim 3 wherein said boom member comprises an intermediate portion interconnecting said first and second portions, said intermediate portion inclining from said first portion toward said stem member to place said second portion in a position proximate and opposed to said guide plug.

5. A drill guide assembly according to claim 3 wherein said second portion of said boom member is provided with a plurality of apertures extending therethrough and adapted to receive said drill bits.

6. A drill guide assembly according to claim 5 wherein said guide plug is provided with recesses for receiving distal ends of said drill bits.

7. A drill guide assembly according to claim 6 wherein each of said second portion apertures is aligned with one of said guide plug recesses.

8. A drill guide assembly according to claim 7 wherein said guide plug recesses comprise annular grooves.

9. A drill guide assembly according to claim 5 wherein said boom member includes an intermediate portion interconnecting said first portion and said second portion, said intermediate portion extending inwardly toward the tunnel.

10. A drill guide assembly according to claim 9 wherein said boom member includes a tray fixed to said second portion and slidably movable on said intermediate portion toward and away from the tunnel, and said intermediate portion is provided with means for releasably locking said tray in place on said intermediate portion.

11. A drill guide assembly according to claim 2 wherein said assembly includes said drill bits, said drill bits including a first drill bit having a first length, and a second drill bit having a second length longer than said first length.

12. A drill guide assembly according to claim 11 wherein said assembly includes said transverse screws, said screws including a compression screw for compressing the bone plug against a wall portion of the tunnel farthest from said second portion of said boom member along the axis of said drill bit, said compression screw having a concave distal end.

13. A drill guide assembly according to claim 11 wherein said assembly includes said transverse screws, said screws including a transfixation screw for fixing the bone plug and ligaments therewith to said wall portion of the tunnel farthest from said second portion of said boom member along the axis of said drill bit, said transfixation screw having a pointed distal end for penetration of the bone plug, the ligaments, and said farthest wall portion.

14. A drill guide assembly according to claim 11 wherein said assembly includes said transverse screws, said screws including a combination transfixation and compression screw for compressing the bone plug against a wall portion of the tunnel farthest from said second portion of said boom member and for fixing ligaments associated with the bone plug to said farthest wall portion, said combination screw having, proximate the distal end thereof, a shoulder for engaging and pressing against the bone plug and ligament, and a pin portion extending distally from said shoulder and pointed at the distal end for penetration of the bone plug, the ligaments, and said farthest wall portion of the tunnel.

15. A drill guide assembly according to claim 2 wherein said second portion of said boom member has a planar configuration.

16. A drill guide assembly according to claim 2 wherein said second portion of said boom member comprises has a first member and a second member, said first and second members being hinged to one another so as to selectively open said apertures for lateral access.

* * * * *